United States Patent [19]

Tadepalli et al.

[11] Patent Number: 5,028,628

[45] Date of Patent: Jul. 2, 1991

[54] METHODS OF TREATING PULMONARY HYPERTENSION

[75] Inventors: Anjaneyulu S. Tadepalli, Durham, N.C.; Brendan J. R. Whittle, Beckenham, England

[73] Assignee: Burroughs Wellcome Co., Research Triangle Park, N.C.

[21] Appl. No.: 421,453

[22] Filed: Oct. 13, 1989

[30] Foreign Application Priority Data

Oct. 14, 1988 [GB] United Kingdom ............... 8824187

[51] Int. Cl.$^5$ ............................................ A61K 31/19
[52] U.S. Cl. ................................. 514/573; 514/530; 514/623
[58] Field of Search ................... 514/573, 530, 623

[56] References Cited

U.S. PATENT DOCUMENTS 4,306,075 12/1981 Aristoff ............................... 560/56

OTHER PUBLICATIONS

Grossman, et al., Pulmonary Hypertension, pp. 835–851, Abnormalities of Circulatory Function.
Ellis, et al., Progress in Medicinal Chemistry, vol. 21, pp. 239–279, 6 Antithrombotic Assessment and Clinical Potential of Prostacyclin Analogues.
Whittle, et al., Platelets and Vascular Occlusion, pp. 1219–1225, vol. 72, No. 6, Dec. 1985, Platelet Actions of Stable Carbocyclic Analogues of Prostacyclin.
Long, et al., Prostacyclin and PGE$_1$ Treatment of Pulmonary Hypertension[1], pp. 773–776, 1987, 136.
Tyle, Pharmaceutical Research, vol. 3, No. 6, 1986, Iontophoretic Devices for Drug Delivery, pp. 318–326.
Whittle, et al., Progress in Medicinal Chemistry, vol. 21, 1984, pp. 237–279, 6 Antithrombotic Assessment and Clinical Potential of Prostacyclin Analogues.
Supplement-Chest, 89, 6, Jun. 1986, 459S, Pulmonary Vascular Disease II, 2:00–3:00 PM.

Primary Examiner—Leonard Schenkman
Attorney, Agent, or Firm—Donald Brown; Lawrence A. Nielsen

[57] ABSTRACT

The present invention is concerned with methods for the treatment and diagnosis of pulmonary hypertension which comprise the administration of an effective amount of a compound of formula (I)

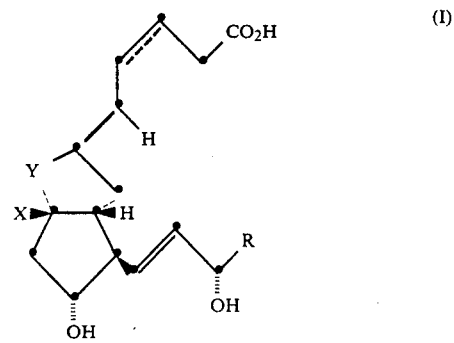

wherein
X is hydrogen or methyl;
Y is —O— or —CH$_2$—;
R is —C(R$^1$)(R$^2$)CH$_2$CH$_2$CH$_2$CH$_3$ wherein R$^1$ and R$^2$, which may be the same or different, are selected from hydrogen and halogen; and
the dotted line represents an optional double bond; and
pharmaceutically acceptable salts and acid derivatives thereof.

Medicaments and diagnostic aids for use in the methods of the invention are also within the scope of the invention.

3 Claims, No Drawings

METHODS OF TREATING PULMONARY HYPERTENSION

The present invention is concerned with prostaglandins, specifically non-benzindene prostaglandins, for use in the treatment, or diagnosis of pulmonary hypertension. Their use in the manufacture of medicaments for the treatment of pulmonary hypertension and in the manufacture of diagnostic aids for identifying PPH patients having active pulmonary vasoconstriction and the medicaments and diagnostic aids obtained thereby are within the scope of the invention.

All blood is driven through the lungs via the pulmonary circulation in order, among other things, to replenish the oxygen which it dispenses in its passage around the rest of the body via the systemic circulation. The flow through both circulations is in normal circumstances equal, but the resistance offered to it in the pulmonary circulation is generally much less than that of the systemic circulation. When the resistance to pulmonary blood flow increases, the pressure in the circulation is greater for any particular flow. This is referred to as pulmonary hypertension. Generally, pulmonary hypertension is defined through observations of pressures above the normal range pertaining in the majority of people residing at the same altitude and engaged in similar activities.

Most often pulmonary hypertension is a manifestation of an obvious or explicable increase in resistance, such as obstruction to blood flow by pulmonary emboli, malfunction of the heart's valves or muscle in handling blood after its passage through the lungs, diminution in pulmonary vessel calibre as a reflex response to hypoventilation and low oxygenation, or a mismatch of vascular capacity and essential blood flow, such as shunting of blood in congenital abnormalities or surgical removal of lung tissue. Such pulmonary hypertension is referred to as secondary hypertension.

There remain some cases of pulmonary hypertension where the cause of the increased resistance is as yet inexplicable. They are described as primary pulmonary hypertension (PPH) and are diagnosed by and after exclusion of the causes of secondary pulmonary hypertension. Despite the possibility of a varied aetiology, cases of primary pulmonary hyptertension tend to comprise a recognisable entity. Approximately 65% are female and young adults are most commonly afflicted, though it has occurred in children and patients over 50. Life expectancy from the time of diagnosis is short, about 3 to 5 years, though occasional reports of spontaneous remission and longer survival are to be expected given the nature of the diagnostic process. Generally, however, progress is inexorable via syncope and right heart failure and death is quite often sudden. Until now, no successful treatment was known.

U.S. Pat. No. 4,306,075 describes a class of novel benzindene prostaglandins which produce various pharmacological responses, such as inhibition of platelet aggregation, reduction of gastric secretion, and bronchodilation. It is indicated that the compounds have useful application as antithrombotic agents, anti-ulcer agents and anti-asthma agents. Non-benzindene prostaglandins having similar properties have also been described (Progress in Medicinal Chemistry, 21, 237 (1984); Circulation, 72, 1219 (1985)). We are not aware of any disclosure to date that benzindene or non-benzindene prostaglandins other than prostacyclin and $PGE_1$ may be used in the treatment, or diagnosis of pulmonary hypertension. We have now unexpectedly found that a class of non-benzindene prostaglandins known for their ability to inhibit platelet aggregation, lower blood pressure and function as anti-ulcer agents are also suitable for use in the treatment of pulmonary hypertension.

The term "pulmonary hypertension" is used herein to include both primary and secondary pulmonary hypertension as ordinarily understood by clinicians (vide supra).

PPH patients having active pulmonary vasoconstriction are considered suitable candidates for long-term oral vasodilator therapy (R J Lambert et al, Chest 89, 459S (1986)). The ability of the compounds of the invention to reduce pulmonary vascular resistance in such patients provides a useful diagnostic aid for identifying suitable candidates for long-term vasodilator therapy. According to the present invention, therefore, there is provided a compound of formula (I)

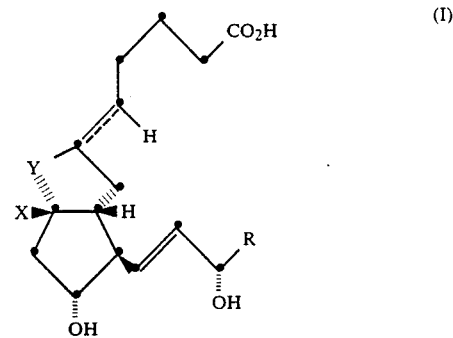

for use in the treatment or diagnosis of pulmonary hypertension wherein

X is hydrogen or methyl;

Y is —O— or —$CH_2$—;

R is —$C(R^1)(R^2)CH_2CH_2CH_2CH_3$ wherein $R^1$ and $R^2$, which may be the same or different, are selected from hydrogen and halogen; and the dotted line represents an optional double bond; and pharmaceutically acceptable salts and acid derivatives thereof.

The term "acid derivative" is used herein to describe $C_{1-4}$ alkyl esters and amides, including amides wherein the nitrogen is optionally substituted by one or two $C_{1-4}$ alkyl groups.

The invention also includes bioprecursors or "prodrugs" of the above-defined compounds, that is, compounds which are converted in vivo to compounds of formula (I) or pharmaceutically active derivatives thereof.

Further aspects of the present invention are concerned with the use of a compound of formula (I), or a pharmaceutically acceptable salt or acid derivative thereof, in the manufacture of a medicament for the treatment of pulmonary hypertension or in the manufacture of a diagnostic aid for identifying PPH patients having active pulmonary vasoconstriction and with medicaments and diagnostic aids obtained thereby which may be administered when primary or secondary pulmonary hypertension is indicated.

Preferred compounds of formula (I) having particularly desirable pulmonary anti-hypertensive properties include those wherein $R^1$ and $R^2$ are both hydrogen or both fluorine; and the optional double bond is present.

A particularly preferred compound of formula (I) having exceptional pulmonary anti-hypertensive properties is (5Z,9S)-9-methyl-6a-carbaprostaglandin $I_2$ which has the following structure:

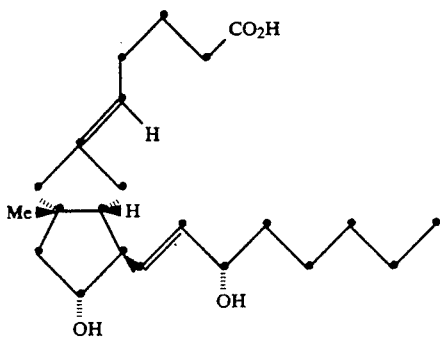

and pharmaceutically acceptable salts and acid derivatives thereof.

The present invention extends to non-physiologically acceptable salts of the compounds of formula (I) which may be used in the preparation of the pharmacologically-active compounds of the invention. The physiologically acceptable salts of compounds of formula (I) include salts derived from organic and inorganic acids as well as from bases. Suitable salts derived from acids include, for example, the acetate, adipate, alginate, aspartate, benzoate, benzenesulphonate, bisulphate, butyrate, citrate, camphorate, camphorsulphonate, cyclopentanepropionate, digluconate, dodecylsulphate, ethanesulphonate, fumarate, glucoheptanoate, glycerophosphate, hemisulphate, heptanoate, hexanoate, hydrochloride, hydrobromide, hydroiodide, 2-hydroxyethanesulphonate, lactate, maleate, methanesulphonate, 2-naphthalenesulphonate, nicotinate, oxalate, palmoate, pectinate, persulphate, 3-phenylpropionate, picrate, pivalate, propionate, succinate, tartrate, thiocyanate, tosylate, and undecanoate.

Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of a compound of formula (I), or a physiologically acceptable salt or acid derivative thereof, which is required in a medication or diagnostic aid according to the invention to achieve the desired effect will depend on a number of factors, in particular the specific application, the nature of the particular compound used, the mode of administration, and the condition of the patient. In general, a daily dose for the treatment of pulmonary hypertension is expected to lie in the range 25 μg to 250 mg, typically from 0.5 μg to 2.5 mg, per day per kilogram bodyweight. For example, an intravenous dose may be in the range 0.5 μg to 1.5 mg/kg/day, which may conveniently be administered as an infusion of from 0.5 ng to 1.0 μg per kilogram per minute. Infusion fluids suitable for this purpose may contain, for example, from 10 ng to 10 μg per milliliter. Ampoules for injection may contain, for example, from 0.1 μg to 1.0 mg and orally administrable unit dose formulations, such as tablets or capsules, may contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from the compound of formula (I).

In the manufacture of a medicament of diagnostic aid according to the invention, hereinafter referred to as a "formulation", the compounds of formula (I) and their physiologically acceptable salts and acid derivatives are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.05% to 95% by weight of the active compound. One or more compounds of formula (I) and/or their physiologically acceptable salts or acid derivatives may be incorporated in the formulations of the invention, which may be prepared by any of the well known techniques of pharmacy consisting essentially of admixing the components.

In addition to compounds of formula (I), other pharmacologically active substances may be present in the formulations of the present invention. For example, the compounds of the invention may be present in combination with tissue plasminogen activator, a substance known to dissolve the fibrin network of blood clots which has found utility in the treatment of thrombotic disorders (see, for example, The New England Journal of Medicine, 312(14), 932, (1985)). The formulations of the invention include those suitable for oral, rectal, topical, buccal (e.g. sub-lingual), parenteral (e.g. subcutaneous, intramuscular, intradermal, or intravenous) and transdermal administration, although the most suitable route in any given case will depend on the nature and severity of the condition being treated and on the nature of the particular compound of formula (I), or the physiologically acceptable salt or acid derivative thereof, which is being used.

Formulations suitable for oral administration may be presented in discrete units, such as capsules, cachets, lozenges, or tablets, each containing a predetermined amount of a compound of formula (I) or a physiologically acceptable salt or acid derivative thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients). In general, the formulations of the invention are prepared by uniformly and intimately admixing the active compound with a liquid or finely divided solid carrier, or both, and then, if necessary, shaping the resulting mixture. For example, a tablet may be prepared by compressing or moulding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding in a suitable machine, the powdered compound moistened with an inert liquid binder.

Formulations suitable for buccal (sub-lingual) administration include lozenges comprising a compound of formula (I), or a physiologically acceptable salt or acid derivative thereof, in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of a compound of formula (I), or a physiologically acceptable salt or acid derivative thereof, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water and rendering the resulting solution sterile and isotonic with the blood. Injectable formulations according to the invention will generally contain from 0.1 to 5% w/w of active compound.

Formulations suitable for rectal administration are preferably presented as unit dose suppositories. These may be prepared by admixing a compound of formula (I), or a physiologically acceptable salt or acid derivative thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w.

Formulations for transdermal administration may be delivered by iontophoresis (see, for example, Pharmaceutical Research 3(6), 318, (1986)) and typically take the form of an optionally buffered aqueous solution of a compound of formula (I) or of a salt or acid derivative thereof.

The compounds of the present invention are conveniently prepared by methods analogous to those described in U.S. Pat. No. 4,306,075.

For a better understanding of the invention, the following Examples are given by way of illustration.

EXAMPLE

The effects of (5Z, 9S)-9-methyl-6a-carba-prostaglandin $I_2$ were monitored in an experimental pulmonary hypertension model. The model used was an open chest preparation of an anaesthesised cat open chest preparation of an anaesthesised cat (anaesthetic: chloralose and urethane). A series of glycine buffer solutions of the test compound were successively administered to each of four animals by i.v. infusion at doses equivalent to 300 ng, 1 mcg, 3 mcg, 10 mcg and 30 mcg/kg/min. Each solution was infused over a period of 20 minutes, hypoxia being induced in the animal during the last 5 minutes of infusion by ventilating with 10% oxygen in nitrogen. A 15-minute 'recovery' period was observed between successive infusions. Following surgery, the animal was allowed to stabilize for 30 minutes, after which two 5-minute hypoxic challenges were given 15 minutes apart which were averaged to obtain the control hypoxic responses. 15 minutes after the second control hypoxic challenge, the animal started to receive the test compound. The averaged control hypoxic responses were compared with those obtained during infusion of the test compound.

The following parameters were monitored during the course of each experiment: systemic arterial pressure (MAP), pulmonary arterial (PAP) and venous (PVP) pressures, and cardiac output (CO, aortic blood flow). From the values obtained, the systemic vascular resistance (MAP/CI where CI=CO/body weight in kg) and the pulmonary vascular resistance (PAP/CI) were calculated.

The test compound was found to reduce hypoxia-induced increase in pulmonary arterial pressure and pulmonary vascular resistance in a dose-related manner without appreciably affecting cardiac output or heart rate. At higher doses, the test compound reduced systemic arterial pressure and systemic vascular resistance. Thus, by suitably adjusting the dose, hypoxia-induced pulmonary vasoconstriction can be reduced without disturbing the systemic haemodynamics. The hypoxia-induced vasoconstriction did not return to its control value within 15 minutes of terminating the final infusion indicating a relatively long duration of action for the compound.

We claim:

1. A method of treating pulmonary hypertension in a patient who is suffering from pulmonary hypertension comprising administering to said patient an effective pulmonary hypertension treatment amount of the compound (5Z, 9S)-9-methyl-6a-carba-prostaglandin $I_2$.

2. A method of treating pulmonary hypertension in a patient who is suffering from pulmonary hypertension comprising administering to said patient an effective pulmonary hypertension treatment amount of a pharmaceutically acceptable salt of the compound (5Z, 9S)-9-methyl-6a-carba-prostaglandin $I_2$.

3. A method of treating pulmonary hypertension in a patient who is suffering from pulmonary hypertension comprising administering to said patient an effective pulmonary hypertension treatment amount of a $C_{1-4}$ alkyl ester or amide of the compound (5Z, 9S)-9-methyl-6a-carba-prostaglandin $I_2$.

* * * * *